United States Patent [19]

Schullmeyer et al.

[11] Patent Number: 5,052,392
[45] Date of Patent: Oct. 1, 1991

[54] CARDIAC SENSING LEAD

[75] Inventors: Michael P. Schullmeyer, Anoka; Lawrence M. Kane, Roseville; James E. Revane, Minnitrista, all of Minn.

[73] Assignee: Angeion Corporation, Plymouth, Minn.

[21] Appl. No.: 479,813

[22] Filed: Feb. 14, 1990

[51] Int. Cl.⁵ .......................... A61B 5/04; A61N 1/04
[52] U.S. Cl. .................. 128/642; 128/419 P; 128/785
[58] Field of Search ............ 128/642, 785, 784, 419 R

[56] References Cited

U.S. PATENT DOCUMENTS

| 3,737,579 | 6/1973 | Bolduc | 128/785 |
| 4,010,758 | 3/1977 | Rockland et al. | 128/785 |
| 4,282,886 | 8/1981 | King | 128/785 |
| 4,355,642 | 10/1982 | Alferness | 128/785 |
| 4,765,341 | 8/1988 | Mower et al. | 128/785 |

FOREIGN PATENT DOCUMENTS 1438810  11/1988  U.S.S.R. .............................. 128/785

Primary Examiner—Lee S. Cohen
Assistant Examiner—K. M. Pfaffle
Attorney, Agent, or Firm—Schwartz & Weinrieb

[57] ABSTRACT

A cardiac sensing lead which is placed and used on the epicardial surface of the heart. The lead consists of a screw-in electrode which acts as the cathode and a mesh of platinum/iridium that acts as the anode. The electrodes' effective distances from each other are no longer than 1cm. The screw-in electrode also acts as the anchor in the tissue and is implanted with a lead applicator. The cardiac sensing lead senses cardiac signals for the application for diagnostic purposes such as for an internal defibrillator or any other external or internal medical devices.

6 Claims, 3 Drawing Sheets

CARDIAC SENSING LEAD

BACKGROUND OF THE INVENTION

1. Field of the Invention

The present invention pertains to a cardiac sensing lead.

2. Description of the Prior Art

Unipolar leads are commonly available in the market. In order to have bipolar leads, the surgeon must implant two unipolar screw-in or stab-in electrodes.

The present invention has two electrodes on the same lead which contacts the cardiac tissue when the lead is screwed into the heart muscle.

SUMMARY OF THE INVENTION

The general purpose of the present invention is a cardiac sensing lead including PI/IR mesh electrode maximally spaced and with a greater surface area in contact with the cardiac tissue for enhanced sensing and stability.

According to one embodiment of the present invention, there is provided a cardiac sensing lead including a low profile body member, a screw-in lead extending downwardly from the body, a circular mesh electrode surrounding the screw-in electrode, and two lead wires connected to the body.

Significant aspects and features of the present invention include a lead for bipolar pacing/sensing cardiac tissue. There is better stability at the lead head due to mesh fibrotic in-growth. The bipolar system also meets requirements for sensing cardiac signals for implantable cardiac defibrillators.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
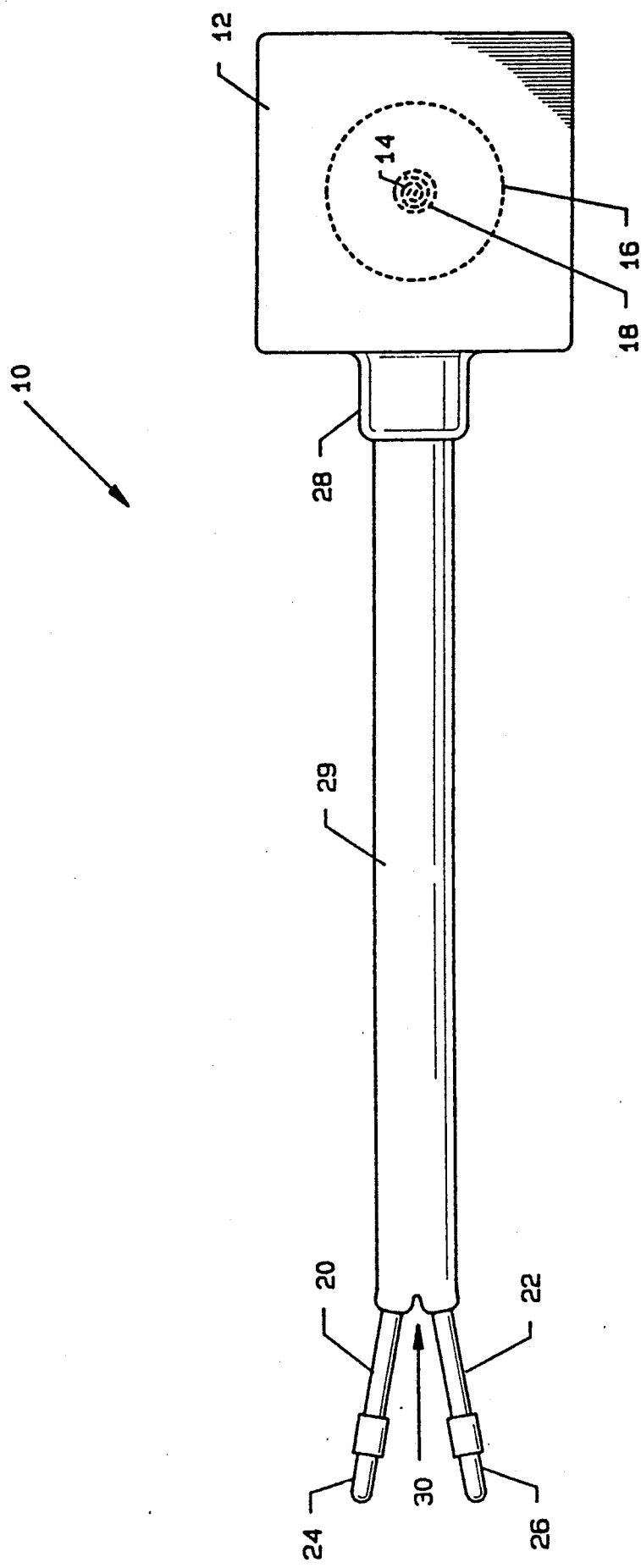
FIG. 1 illustrates a plane view of the cardiac sensing lead, the present invention.

FIG. 1 illustrates a plan view of a cardiac sensing lead 10, the present invention, including a low profile body 12 which is an insulated housing, a screw-in helical electrode 14 supported in the low profile body 12 and extending from a bottom side, a circular mesh electrode 16 with a central hole 18 supported on the underside of the low profile body 12 and about the screw-in helical electrode 14, and insulated conductor wires 20 and 22 connected between the electrodes 14 and 16 to terminal pins 24 and 26. The two insulated conductor wires 20 and 22 can be combined into a single lead 29 between strain relief 28 and a Y junction 30 or in the alternative, an inline bipolar connector.

Figure 2:
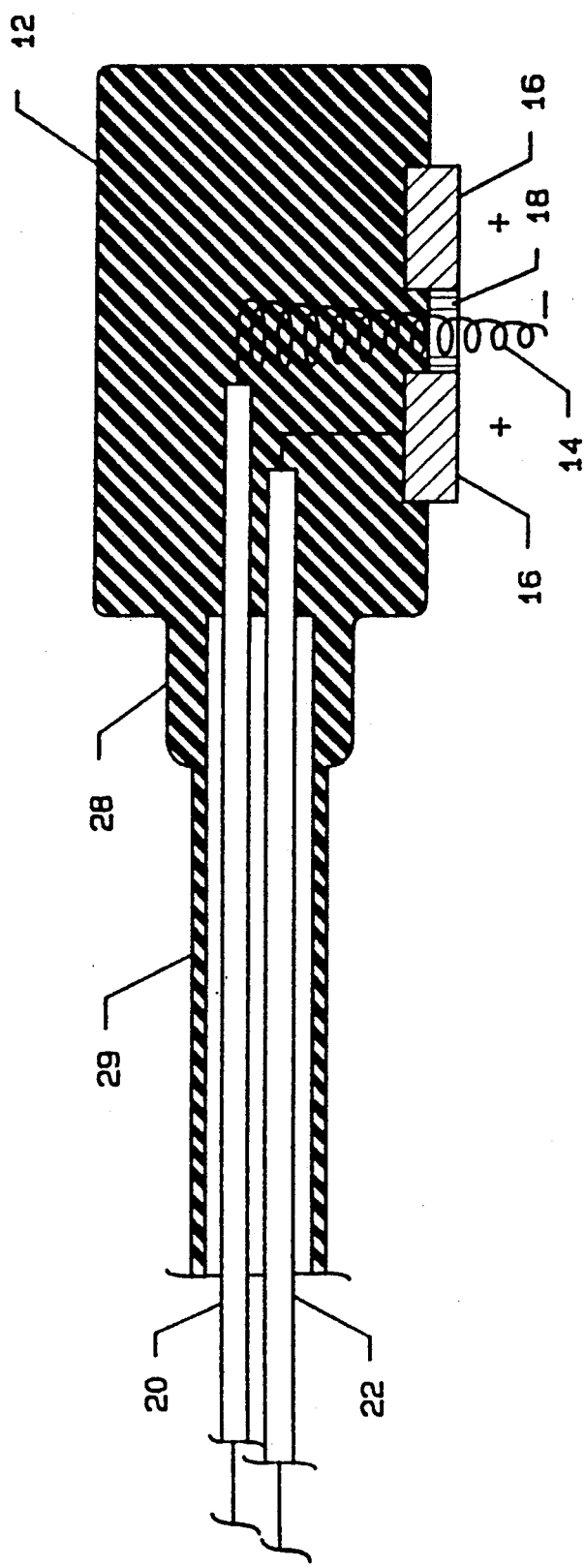
FIG. 2 illustrates a side view in cross section of the cardiac sensing lead; and, FIG. 3 illustrates a bottom view of the cardiac sensing lead.

FIG. 2 illustrates a side view in cross section of the cardiac sensing lead 10 where all numerals correspond to those elements previously described.

Figure 3:
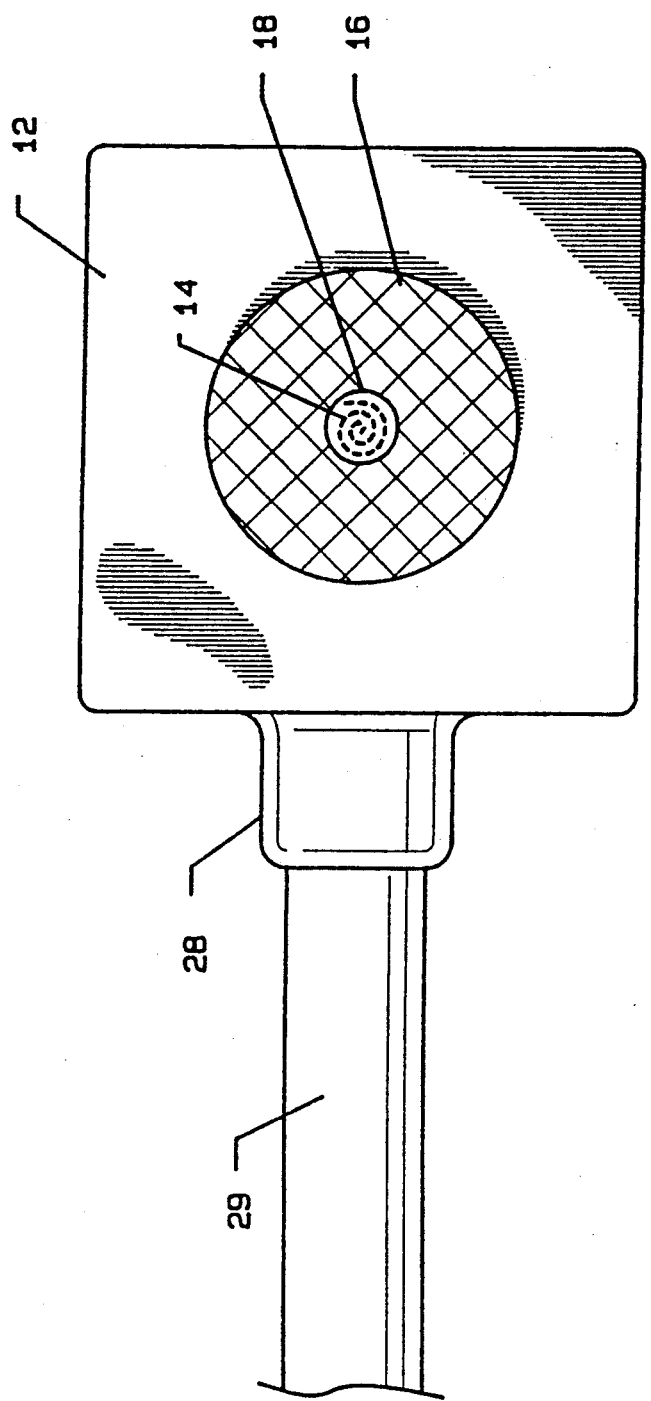

FIG. 3 illustrates a bottom view of the cardiac sensing lead 10 where all numerals correspond to those elements previously described.

MODE OF OPERATION

The cardiac sensing lead 10 is screwed into an area of the heart that is avascular. The cardiac sensing lead 10 is turned in a clockwise rotation to allow the helical screw and electrode 14 to engage the heart tissue. When the screw is at its maximum distance, the mesh electrode 16 is then in contact with the surface of the heart. The cardiac sensing lead 10 is positioned accordingly for the particular application in the thoracic cavity. The mesh has a two-fold purpose, the first purpose is for cardiac signal sensing and can also be used for cardiac pacing and the second purpose is for fibrotic ingrowth. The helical screw and the wire mesh electrodes can be connected in either polarity, but generally the helical screw and electrode is connected to a negative polarity and the wire mesh is connected to a positive polarity.

Various modifications can be made to the present invention without departing from the apparent scope hereof.

I claim:

1. A cardiac sensing lead, comprising:
   an insulated housing having one surface thereof provided for disposition toward the heart of a patient;
   an electrically conductive helical means mounted within said insulated housing and projecting outwardly from said one surface of said insulated housing for threaded engagement within said heart of said patient so as to mount said cardiac sensing lead upon said heart of said patient;
   means defining a recess within said one surface of said insulated housing;
   an electrically conductive mesh means mounted within said recess means of said insulated housing so as to be partially embedded within said insulated housing, so as to provide said insulated housing with a small cross-sectional profile, while being electrically insulated from said electrically conductive helical means and to project partially outwardly beyond said one surface of said insulated housing so as to be disposed in contact with a surface portion of said heart of said patient so as to promote growth of tissue from said heart of said patient so as to securely maintain said cardiac sensing lead mounted upon said heart of said patient;
   a first electrical conductor electrically connected to said electrically conductive helical means; and
   a sound electrical conductor electrically connected to said electrically conductive mesh means.

2. A cardiac sensing lead as set forth in claim 1, wherein:
   said mesh means has a substantially circular configuration.

3. A cardiac sensing lead as set forth in claim 2, wherein:
   said means defining said recess has a substantially circular configuration corresponding to that of said mesh means so as to house said mesh means.

4. A cardiac sensing lead as set forth in claim 2, wherein:
   said mesh means comprises an annulus annularly surrounding said helical means.

5. A cardiac sensing lead as set forth in claim 1, wherein:
said first electrical conductor and said second electrical conductor are electrically insulated from each other so that said helical means may be electrically connected within an electrical circuit so as to have a negative polarity; and
said mesh means may be electrically connected within said electrical circuit so as to have a positive polarity.

6. A cardiac sensing lead as set forth in claim 1, wherein:
said mesh means comprises platinum/iridium.

* * * * *